(12) United States Patent
Helfert et al.

(10) Patent No.: US 6,888,006 B2
(45) Date of Patent: May 3, 2005

(54) METHOD FOR PROCESSING PYROLLIDONE AND N-VINYL PYROLLIDONE RESIDUES

(75) Inventors: Herbert Helfert, Frankenthal (DE); Martin Schmidt-Radde, Beindersheim (DE); Gerhard Laqua, Kapellen (BE); Ulrich Eiden, Kindenheim (DE); Stephan Scholl, Bad Dürkheim (DE); Christoph Übler, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 178 days.

(21) Appl. No.: 10/275,564

(22) PCT Filed: May 10, 2001

(86) PCT No.: PCT/EP01/05351

§ 371 (c)(1),
(2), (4) Date: Nov. 7, 2002

(87) PCT Pub. No.: WO01/85682

PCT Pub. Date: Nov. 15, 2001

(65) Prior Publication Data

US 2003/0105338 A1 Jun. 5, 2003

(51) Int. Cl.$^7$ ............................................ C07D 207/267

(52) U.S. Cl. ...................................................... 548/555
(58) Field of Search .......................................... 548/555

(56) References Cited

U.S. PATENT DOCUMENTS

| | | | | |
|---|---|---|---|---|
| 3,975,400 | A | | 8/1976 | Himmele et al. ............ 260/326 |
| 4,410,726 | A | | 10/1983 | Parthasarathy et al. ..... 548/543 |
| 4,892,624 | A | * | 1/1990 | Fuchs ........................... 203/37 |
| 4,939,273 | A | * | 7/1990 | Liu et al. ..................... 548/543 |
| 5,393,888 | A | | 2/1995 | Mimmock et al. ........... 548/554 |
| 5,441,607 | A | | 8/1995 | Fuchs et al. ................... 203/49 |
| 6,703,511 | B2 | * | 3/2004 | Eck et al. ..................... 548/543 |

FOREIGN PATENT DOCUMENTS

| | | |
|---|---|---|
| DE | 1 795 007 | 1/1972 |
| DE | 32 15 093 | 1/1983 |
| EP | 0 633 246 | 1/1995 |
| GB | 799924 | 8/1958 |

\* cited by examiner

Primary Examiner—Johann Richter
Assistant Examiner—Ebenezer Sackey
(74) Attorney, Agent, or Firm—Novak, Druce, DeLuca & Quigg

(57) ABSTRACT

A process for working up residues from the preparation of pyrrolidone and/or N-vinylpyrrolidone comprises subjecting the residues to a thermolysis.

7 Claims, 1 Drawing Sheet

METHOD FOR PROCESSING PYROLLIDONE AND N-VINYL PYROLLIDONE RESIDUES

Figure 1:
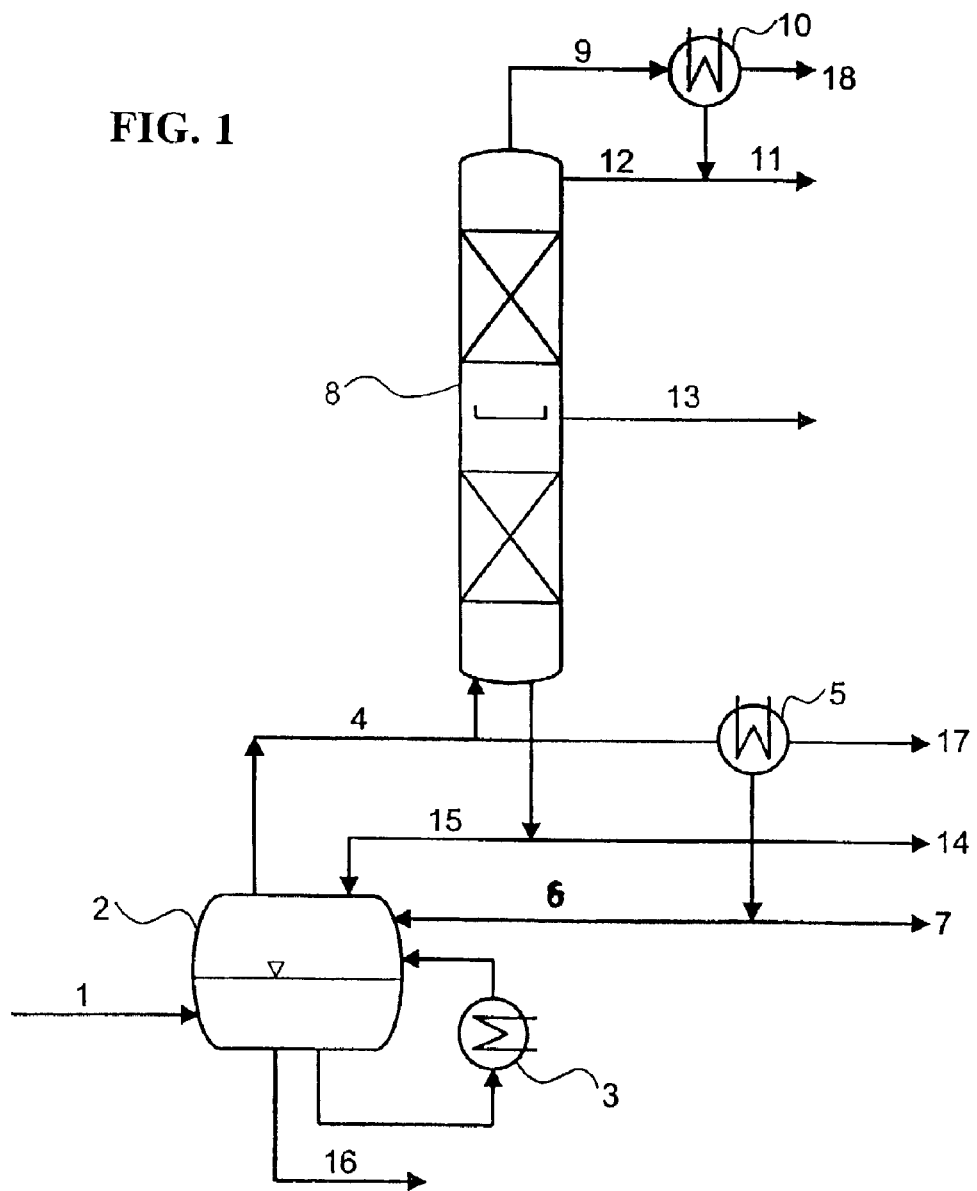

The present invention relates to a process for working up residues from the preparation of pyrrolidone and/or N-vinylpyrrolidone.

Pyrrolidone is synthesized industrially by reaction of butyrolactone with ammonia. It is used mainly as intermediate for the synthesis of N-vinylpyrrolidone, in which pyrrolidone is reacted with the ethyne to give N-vinylpyrrolidone. N-vinylpyrrolidone is used for the preparation of polyvinylpyrrolidone which is employed as auxiliary in cosmetics and pharmacy.

The residues from pyrrolidone and N-vinylpyrrolidone production have hitherto been disposed of by incinerating them in the presence of oxygen. Prior recovery of pyrrolidone and N-vinylpyrrolidone from the residues to be disposed of has hitherto been technically difficult and not economically feasible.

It is an object of the present invention to provide a process for working up pyrrolidone and N-vinylpyrrolidone residues which makes it possible to recover pyrrolidone and N-vinylpyrrolidone from the residues in an economical manner.

We have found that this object is achieved by subjecting the residues from pyrrolidone and N-vinylpyrrolidone production either individually or combined to a thermolysis. It has surprisingly been found that more pyrrolidone and/or N-vinylpyrrolidone than was previously present in the respective residues can be formed and separated off, as a result of which the amount of remaining final residues is considerably reduced.

The present invention accordingly provides a process for working up residues from the preparation of pyrrolidone and/or N-vinylpyrrolidone, which comprises subjecting the residues to a thermolysis. Particular preference is given to working up the combined residues from the preparation of pyrrolidone and N-vinylpyrrolidone. Preferred embodiments of the invention are indicated in the following description, the FIGURE, the example and the subordinate claims.

The single FIGURE shows a preferred embodiment of the invention with distillation and/or condensation following the thermolysis.

In the present text, the term "pyrrolidone" refers to the compound 2-pyrrolidone, also known as butyrolactam. "N-vinylpyrrolidone" in the present text refers to the compound N-vinyl-2-pyrrolidone (or N-vinylbutyrolactam).

The residues which can be worked up using the process of the present invention are subject to no particular restrictions. All residues obtained in the preparation of pyrrolidone or N-vinylpyrrolidone after they have been separated from the synthesis product are suitable.

Pyrrolidone is advantageously prepared industrially by reaction of γ-butyrolactone with ammonia in the presence of water at elevated pressure and elevated temperature, for example 240° C., with virtually quantitative conversion. The ammonia, which is used in excess, and water are separated off after the synthesis and returned to the synthesis. A two-stage distillation is then advantageously carried out to isolate the desired product pyrrolidone. In the first stage, low boilers, i.e. components which boil at a lower temperature than does pyrrolidone, for example water, amine components and butyrolactone, are separated off. In the second stage, nonvolatile components or high boilers, i.e. compounds which have a boiling point higher than that of pyrrolidone, are separated off in a thin film evaporator. Here, the desired product pyrrolidone is obtained at the top in a purity of generally more than 99.5% (pure pyrrolidone), while the bottom product comprising the nonvolatile components and high boilers together with residual amounts of pyrrolidone represents the pyrrolidone residue to be disposed of, which can be worked up according to the present invention.

To synthesize N-vinylpyrrolidone, the pure pyrrolidone is subsequently vinylated by means of ethyne in the presence of a suitable vinylation catalyst, for example pyrrolidonepotassium, at a partial conversion of from 20 to 70%. The vinylation reaction with the ethyne is preferably carried out in a pressure reactor. Subsequently, a two-stage distillation is advantageously carried out to isolate the N-vinylpyrrolidone from the synthesis product. In the first distillation stage, preferably under reduced pressure and at elevated temperature, preferably from 150 to 160° C., the low boilers, i.e. the compounds which have a boiling point lower than the boiling point of N-vinylpyrrolidone, in particular excess ethyne, water and amine components, are separated off. The bottom product from the first distillation stage is passed to the second distillation stage. In the second distillation stage, an N-vinylpyrrolidone having a purity of about 90% (crude N-vinylpyrrolidone) is obtained as top product and can be purified further to a desired degree of purity. The bottom product from the second distillation stage comprises the nonvolatile components and high boilers, i.e. compounds having a boiling point higher than the boiling point of N-vinylpyrrolidone, together with pyrrolidone and residual N-vinylpyrrolidone. The bottom product from the second distillation stage is, either wholly or in part, passed to a third distillation stage which is carried out in a thin film evaporator. The bottom product from the third distillation stage represents N-vinylpyrrolidone residue to be disposed of, which can be worked up according to the present invention. Furthermore, unreacted pyrrolidone is also separated off in the third distillation stage and is returned to the vinylation reaction.

The pyrrolidone residue is preferably a residue which has the composition of a bottom product obtained by reaction of γ-butyrolactone and ammonia to give pyrrolidone after work-up by distillation, in particular as described above. Correspondingly, the N-vinylpyrrolidone residue is preferably a residue having the composition of a bottom product obtained by reaction of pyrrolidone with ethyne to give N-vinylpyrrolidone after work-up by distillation, in particular as described above. Particularly suitable pyrrolidone residues comprise from 0 to 10% by weight, in particular from 3.2 to 4.1% by weight, of pyrrolidone, from 0.2 to 3% by weight, in particular from 0.8 to 1.2% by weight, of 4-(N-pyrrolidono)-n-butyronitrile, from 3 to 15% by weight, in particular about 5% by weight, of sodium and, as remainder, organic components, for example oligomers and polymers of pyrrolidone and organic anions of the salts, in each case based on 100% by weight of pyrrolidone residue. Particularly suitable N-vinylpyrrolidone residues comprise from 0 to 10% by weight, in particular from 1 to 4% by weight, of N-vinylpyrrolidone, from 10 to 70% by weight, in particular from 40 to 60% by weight, of pyrrolidone, from 0 to 10% by weight, in particular from about 1 to 4% by weight, of ethylidene-N,N'-bispyrrolidone, from 0 to 5% by weight, in particular from 1 to 3% by weight, of 4-(N-pyrrolidono)-n-butyronitrile and, as remainder, organic components, for example oligomers and polymers of pyrrolidone and/or vinylpyrrolidone, organic anions of salts, in each case based on 100% by weight of N-vinylpyrrolidone residue. The pyrrolidone and N-vinylpyrrolidone residues can be subjected to the process of the present invention either individually or as mixtures, with the use of mixed residues being particularly preferred. When mixed residues are used, they are preferably used in a ratio of pyrrolidone residue to N-vinylpyrrolidone residue of from 0.05:1 to 2:1, in particular from 0.1:1 to 0.3:1, with a ratio of 20% by weight of pyrrolidone residue and 80% by weight of N-vinylpyrrolidone residue, in each case based on 100% by weight of mixed residue, being most preferred. Thus, a particularly suitable mixed residue has the following composition, in each case based on 100% by weight of mixed residue: from 1 to 20% by weight, in particular from 4.5 to 13% by weight, of pyrrolidone; less than 10% by weight, in particular less than 1% by weight, of N-vinylpyrrolidone; from 0 to 10% by weight, in particular from 3.0 to 6.0% by weight, of ethylidene-N,N'-bispyrrolidone; from 0 to 8% by weight, in particular from 1.0 to 4.0% by weight, of 4-(N-pyrrolidono)-n-butyronitrile; from 0.5 to 4% by weight, in particular about 2% by weight, of sodium (ions); from 5 to 20% by weight, in particular about 8% by weight, of potassium (ions); and, as remainder, in particular from 67 to 80% by weight of organic components, for example oligomers and polymers of pyrrolidones and anions of the salts.

The thermolysis carried out according to the present invention is the decomposition of compounds under the action of thermal energy, which can, under relatively severe temperature conditions, also be referred to as pyrolysis. The conditions under which the thermolysis is carried out according to the present invention are subject to no particular restrictions. The thermolysis is carried out at elevated temperature, in particular at a temperature in the range from 180 to 250° C., particularly preferably from 200 to 230° C. The thermolysis is advantageously carried out under reduced pressure, in particular at from 1 to 50 mbar absolute, particularly preferably from 5 to 20 mbar absolute. Suitable residence times can easily be determined by a person skilled in the art; a residence time, in each case based on the residues used, of from 1 to 10 hours, preferably from 3 to 5 hours, has been found to be advantageous.

The reactors suitable for carrying out the thermolysis are likewise subject to no particular restrictions. All reactors known to those skilled in the art for this field are suitable. Particularly suitable reactors are stirred reactors or residence time vessels with pumped circulation, since these ensure good mixing. Combinations of residence time vessels and thin film evaporators are most preferred as thermolysis reactors. Reactors having heated, self-cleaning stirrers (Discotherm, Liszt-Dryer) are also suitable. The thermolysis can be carried out continuously or batchwise, preferably continuously.

In an advantageous embodiment of the invention, the stream of vapor formed in the thermolysis is subjected to a distillation or rectification after and/or during the thermolysis. The columns suitable for this purpose are subject to no restrictions.

For example, it is possible to use columns with ordered packing, columns with random packing or tray columns. The top product from the distillation or rectification can be condensed, with part of the condensate being able to be discharged and the remainder returned to the column as run back. The desired product, i.e. the pyrrolidone or N-vinylpyrrolidone, can be taken off either at a side offtake or as bottom product, with part of the bottoms being able to be returned to the thermolysis reactor in order to hold back undesirable high-boiling components. In a further, preferred embodiment of the invention, the vapor formed in the thermolysis is condensed in a condenser, with part of the condensate obtained being able to be returned to the thermolysis reactor or being able to be taken off as desired product and, if desired, worked up further. It is also possible to condense only part of the vapor from the thermolysis reaction and pass the remainder to a distillation or rectification as described above.

In a further, preferred embodiment, the residue remaining after and/or in the thermolysis is discharged from the reactor and disposed of in a suitable manner, for example incinerated after dilution with a suitable diluent to lower the viscosity.

The process of the present invention makes it possible to recover, based on 100% by weight of residues used, from 15 to 40% by weight, in particular from 20 to 30% by weight, of pyrrolidone and/or N-vinylpyrrolidone having a purity of at least 95% by weight, based on the total distillate from the thermolysis reaction. It has surprisingly been found that the process of the present invention yields not only the amounts of pyrrolidone and/or N-vinylpyrrolidone present in the residues but, in addition, considerable additional amounts of pyrrolidone and/or N-vinylpyrrolidone are formed. Thus, more desired product can be separated off by means of the process of the present invention than was originally present in the residues. This leads to a considerable reduction in the amounts of remaining residue to be disposed of. Thus, the process of the present invention leads to considerable cost savings in the disposal of pyrrolidone and/or N-vinylpyrrolidone residues.

The FIGURE shows a preferred process according to the present invention with distillation and/or condensation following thermolysis. The residues 1 are fed to the thermolysis reactor 2, for example a thermolysis pot. The thermolytic reaction of the residues takes place there under reduced pressure and at elevated temperature by means of heat input from the vaporizer 3, preferably a circulation vaporizer. The vapor 4 formed can be condensed partly or completely in a condenser 5 under vacuum 17. The condensate obtained can be partly returned via line 6 to the thermolysis reactor 2 and/or taken off as desired product via line 7 and, if appropriate, worked up further. Alternatively, all or part of the vapor 4 formed in the thermolysis reaction can be passed to a rectification column 8, which is preferably a normal column with ordered packing. The vapor 9 leaving the column at the top is condensed in a condenser 10 via vacuum 18. Part of the condensate can be discharged as top product 11 while the remainder can be returned to the column 8 as run back 12. The desired product stream, comprising the desired pyrrolidone and/or N-vinylpyrrolidone, can be taken off at the side offtake 13 or from the bottom of the column via line 14. When the desired product stream is taken off at a side offtake, the purity of the desired product is higher and is generally at least 95% by weight of pyrrolidone and 3% by weight of vinylpyrrolidone. The remaining column bottoms 15 are returned to the thermolysis reactor 2 to hold back interfering high-boiling components. The residue remaining after the thermolysis is discharged via line 16 and disposed of.

The invention is illustrated by the following example, which represents a preferred embodiment of the invention.

EXAMPLE

Experiments were carried out using three different residues, namely a pyrrolidone residue, an N-vinylpyrrolidone residue and combined pyrrolidone and N-vinylpyrrolidone residues. The composition of the pyrrolidone residue was as following, in each case based on 100% by weight of the pyrrolidone residue:
    from 3.2 to 4.1% by weight of pyrrolidone,
    from 0.8 to 1.2% by weight of 4-(N-pyrrolidono)-n-butyronitrile,
    about 5% by weight of sodium (ions) and,
    as remainder, organic components not detectable by gas chromatography (e.g. oligomers and polymers of pyrrolidone, organic anions of the salts).

The composition of the N-vinylpyrrolidone residue, in each case based on 100% by weight of the N-vinylpyrrolidone residue, was as follows:
    about 0.11% by weight of N-vinylpyrrolidone,
    about 7.5% by weight of pyrrolidone,
    about 6.4% by weight of ethylidene-N,N'-bispyrrolidone,
    about 0.9% by weight of 4-(N-pyrrolidono)-n-butyronitrile and,
    as remainder, organic components not detectable by gas chromatography (e.g. oligomers and polymers of pyrrolidone or vinylpyrrolidone, organic anions of the salts).

The composition of the combined pyrrolidone and N-vinylpyrrolidone residue, in each case based on 100% by weight of combined residue, was as follows:
    from 4.5 to 13% by weight of pyrrolidone,
    less than 0.1% by weight of N-vinylpyrrolidono,
    from 3.0 to 6.0% by weight of ethylidene-N,N'-bispyrrolidone,
    from 1.0 to 4.0% by weight of 4-(N-pyrrolidono)-n-butyronitrile,
    about 2% by weight of sodium (ions),
    about 8% by weight of potassium (ions) and
    from 67 to 80% by weight of organic components not detectable by gas chromatography (e.g. oligomers and polymers of pyrrolidone and vinylpyrrolidone, organic anions of the salts).

The residues were subjected to thermolysis with simultaneous distillation under identical conditions in respect of pressure, temperature, residence time and mixing, which was carried out as follows.

1500 g of fresh residue (at about 130° C.) were weighed into a 2l four-neck flask fitted with metal stirrer. A packed column (height: 20 cm; diameter: 3 cm) with 5 mm glass rings, manually controlled column top and 500 ml distillate receiver (single-neck flask) was superposed on the four-neck flask and the residue was heated to 160–170° C. by means of an oil bath (silicone oil). The metal stirrer was then brought into operation and a 1–3 mbar vacuum was carefully applied by means of a rotary vane vacuum pump. The temperature was slowly increased further until satisfactory reflux was established at the top of the column. After one hour under total reflux, a first fraction was distilled off at a reflux ratio of 3:1. The distillation of the first fraction was stopped as soon as no more distillate went over at a temperature at the bottom of about 220° C. To isolate a second fraction, the temperature at the bottom was reduced to about 180° C. by lowering the oil bath, the vacuum was broken by means of nitrogen and the column was replaced by a simple distillation attachment (Claisen attachment with Liebig condenser) with 250 ml distillate receiver. After again applying a 1–3 mbar vacuum, the second fraction was distilled off to a final temperature at the bottom of about 240° C.

The two fractions obtained from the respective residues were analyzed, giving the yields of desired products shown in the table below. In the table, the total distillate based on the amount of residue used, the desired product concentration found in the distillate and the corresponding desired product yields are reported. All results are based on the sum of the respective first and second fractions.

TABLE

Thermolysis of various residues

|  | Pyrrolidone residue | N-vinyl-pyrrolidone residue | Combined pyrrolidone and N-vinylpyrrolidone residues |
| --- | --- | --- | --- |
| Total distillate [% by weight] | 38 | 31.2 | 35.8 |
| γ-butyrolactone [% by weight] | 7.9 | – | – |
| Pyrrolidone [% by weight] | 37.1 | 73.4 | 69.8 |
| N-vinylpyrrolidone [% by weight] | — | 10.0 | 10.3 |
| Σ others [% by weight] | 55.0 | 16.6 | 19.9 |
| Desired product yield [% by weight] | 17.1 | 26.0 | 28.7 |

As can be seen from the table, considerably more desired product(s) than was expected according to the quantitative analyses of the respective starting material was/were distilled off in the case of all residues. Thus, in the case of the combined residue, the amounts of pyrrolidone and N-vinylpyrrolidone distilled off corresponded to a pyrrolidone content of 25% and an N-vinylpyrrolidone content of 3.7%, in each case based on the combined residue used. Since, however, the residue used contained less than 13% by weight of pyrrolidone and less than 0.1% by weight of vinylpyrrolidone, the difference, which was at least twice the amounts expected, corresponded to desired product formed during the thermolysis.

We claim:

1. A process for working up residues from the preparation of pyrrolidone and/or N-vinylpyrrolidone, which comprises combining a residue from the preparation of pyrrolidone and a residue from the preparation of N-vinylpyrrolidone to obtain combined residues, and subjecting the combined residues to a thermolysis, which is carried out at a residence time, based on the residues used, of from 1 to 10 hours.

2. A process as claimed in claim 1, wherein the residue from the preparation of pyrrolidone has the composition of a bottom product obtained by reaction of γ-butyro-lactone and ammonia to give pyrrolidone, and the residue from the preparation of N-vinylpyrrolidone has the composition of a bottom product obtained by reaction of pyrrolidone and ethylene, in each case after purification by distillation.

3. A process as claimed in claim 1, wherein the residues are combined in a ratio of pyrrolidone residue to N-vinylpyrrolidone residue of from 0.05:1 to 2:1.

4. A process as claimed in claim 1, wherein the thermolysis is carried out at from 180 to 250° C.

5. A process as claimed in claim 1, wherein the thermolysis is carried out at a pressure in the range from 1 to 50 mbar absolute.

6. A process as claimed in claim 1, wherein the vapor formed in the thermolysis is subjected to a distillation or rectification.

7. A process as claimed in claim 1, wherein the vapor formed in the thermolysis is subjected to a condensation.

* * * * *